US010376491B2

(12) United States Patent
Yan et al.

(10) Patent No.: US 10,376,491 B2
(45) Date of Patent: Aug. 13, 2019

(54) PHARMACEUTICAL COMPOSITION CONTAINING SILIBININ AND PUERARIA ROOT EXTRACT

(71) Applicant: TASLY PHARMACEUTICAL GROUP CO., LTD., Tianjin (CN)

(72) Inventors: Xijun Yan, Tianjin (CN); Naifeng Wu, Tianjin (CN); He Sun, Tianjin (CN); Kaijing Yan, Tianjin (CN); Yonghong Zhu, Tianjin (CN); Xiaohui Ma, Tianjin (CN); Shunnan Zhang, Tianjin (CN); Changwen Li, Tianjin (CN); Xiaolin Bai, Tianjin (CN); Ting Li, Tianjin (CN); Lei Li, Tianjin (CN); Yi He, Tianjin (CN)

(73) Assignee: Tasly Pharmaceutical Group Co., Ltd., Tianjin (CN)

( * ) Notice: Subject to any disclaimer, the term of this patent is extended or adjusted under 35 U.S.C. 154(b) by 0 days.

(21) Appl. No.: 15/560,583

(22) PCT Filed: Mar. 22, 2016

(86) PCT No.: PCT/CN2016/077038
§ 371 (c)(1),
(2) Date: Sep. 22, 2017

(87) PCT Pub. No.: WO2016/150379
PCT Pub. Date: Sep. 29, 2016

(65) Prior Publication Data
US 2018/0104216 A1 Apr. 19, 2018

(30) Foreign Application Priority Data
Mar. 23, 2015 (CN) .......................... 2015 1 0128638

(51) Int. Cl.
| *A61K 36/00* | (2006.01) |
| *A61K 31/357* | (2006.01) |
| *A61K 36/82* | (2006.01) |
| *A61K 47/24* | (2006.01) |
| *A61K 9/48* | (2006.01) |
| *A61K 31/205* | (2006.01) |
| *A61P 1/16* | (2006.01) |
| *A61K 9/16* | (2006.01) |
| *A61K 31/355* | (2006.01) |
| *A61K 31/683* | (2006.01) |
| *A61K 9/08* | (2006.01) |
| *A61K 36/488* | (2006.01) |

(52) U.S. Cl.
CPC .............. *A61K 31/357* (2013.01); *A61K 9/08* (2013.01); *A61K 9/1617* (2013.01); *A61K 9/1682* (2013.01); *A61K 9/48* (2013.01); *A61K 31/205* (2013.01); *A61K 31/355* (2013.01); *A61K 31/683* (2013.01); *A61K 36/488* (2013.01); *A61K 36/82* (2013.01); *A61K 47/24* (2013.01); *A61P 1/16* (2018.01); *A61K 2236/19* (2013.01)

(58) Field of Classification Search
CPC ...................................................... A61K 36/00
See application file for complete search history.

(56) References Cited

FOREIGN PATENT DOCUMENTS

| BY | 17987 C1 | 2/2014 |
| CN | 1961874 A | 5/2007 |
| CN | 101926791 A | * 12/2010 |
| CN | 101961059 A | 2/2011 |
| CN | 101961060 A | 2/2011 |
| CN | 101961061 A | 2/2011 |
| CN | 101961425 A | 2/2011 |
| CN | 102960500 A | 3/2013 |
| CN | 103230432 A | 8/2013 |
| CN | 103372169 A | 10/2013 |
| CN | 103623046 A | 3/2014 |
| CN | 103655929 A | 3/2014 |
| CN | 103751798 A | 4/2014 |
| CN | 103830204 A | 6/2014 |
| EP | 0209037 A1 | 1/1987 |
| RU | 2314797 C2 | 1/2008 |
| RU | 2318538 C1 | 3/2008 |

OTHER PUBLICATIONS

Sun et al, History of Pu'er Tea and comparative study for the effect of its various extracts on lipid-lowering diet. Pakistan journal of pharmaceutical sciences, (Jul. 2014) vol. 27, No. 4 Suppl, pp. 1015-1022 (Year: 2014).*
Qiong et al, History of Pu'er Tea and comparative study for the effect of its various extracts on lipid-lowering diet. Pakistan journal of pharmaceutical sciences, (Jul. 2014) vol. 27, No. 4 Suppl, pp. 1015-1022 (Year: 2014).*
Lim et al, Effects of dietary isoflavones from Puerariae radix on lipid and bone metabolism in ovariectomized rats. Nutrients (2013), vol. 5, No. 7, pp. 2734-2746, 41 (Year: 2013).*
Yang et al. "Study on the treatment of non-alcoholic fatty liver disease"; Jilin Journal of Traditional Chinese Medicine; vol. 31 No. 7; 2011; p. 621-622 (English Translation).
International Patent Application No. PCT/CN2016/077038; Int'l Written Opinion and Search Report; dated Jun. 16, 2016; 8 pages.
Matteucci et al.; "Liver Disease in Diabetes Mellitus: Potential Therapeutic Value of Vitamin E-Silybin Phytosomal Complex"; Immunology, Endocrine and Metabolic Agents in Medicinal Chem; vol. 10 No. 2; 2010; p. 84-90.
Liu et al.; "Clinical Effect of Silymarin Combined with Levocarnitine on Nonalcoholic Fatty Liver Disease"; China Modern Medicine; vol. 16 No. 7; Apr. 2009; p. 19-20 (abstract).
Falasca et al.; "Treatment with Silybin-Vitamin E-Phospholipid Complex in Patients with Hepatitis C Infection"; Journal of Medical Virology; vol. 80; 2008; p. 1900-1906.

(Continued)

*Primary Examiner* — Qiuwen Mi
(74) *Attorney, Agent, or Firm* — Baker Hostetler

(57) ABSTRACT

Disclosed are a pharmaceutical composition for treating non-alcoholic fatty liver and a method for preparing same. The composition is prepared from the following hulk drugs by weight ratio: 8.75-60 parts of silibinin, 15-65 parts of phospholipid, 25-200 parts of Pu'er tea extract, and 5-50 parts of radix puerariae extract.

20 Claims, 1 Drawing Sheet

(56) References Cited

OTHER PUBLICATIONS

WPI Database; No. 2013-J59447; Menghai Tea Ind Co. Ltd.; Mar. 2013; 2 pages.
Koo et al.; "Effects of Camellia sinensis Extracts on the Antioxidant System and Alcohol Down-Regulation Enzymes in Sub-Acute Ethanol Treated ICR Mice"; Journal of the Korean Society of Food Science and Nutrition; vol. 36 No. 9; 2007; p. 1134-1139 (abstract only); 4 pages.
Grattagliano et al.; "A silybin-phospholipids complex counteracts rat fatty liver degeneration and mitochondrial oxidative changes"; World Journal of Gastroenterolgy; vol. 19 No. 20; May 2013; p. 3007-3017.
Abascal et al.; "Kudzu—the Miracle Vine"; Alternative & Complementary Therapies; vol. 13; Apr. 2007; p. 78-85.

\* cited by examiner

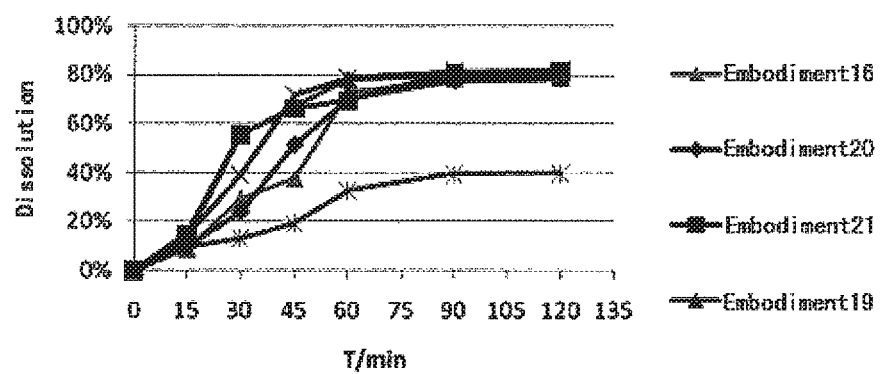
Dissolution curves of different prescriptions of silibinin-phospholipid-Pu'er tea-pueraria root extract preparation in the solution at pH1.2

PHARMACEUTICAL COMPOSITION CONTAINING SILIBININ AND PUERARIA ROOT EXTRACT

CROSS-REFERENCE TO RELATED APPLICATIONS

This application is the National Stage of International Application No. PCT/CN2016/077038 filed Mar. 22, 2016, which claims the benefit of Chinese application number 201510128638.8, filed Mar. 23, 2015 the disclosures of which are incorporated herein by reference in their entireties.

TECHNICAL FIELD

The present invention relates to the technical field of medicines, and particularly to a pharmaceutical composition containing silibinin far the treatment of hepatopathy.

BACKGROUND ART

In the late 1960s and 1980s, the pharmaceutists of West Germany with H.wagner as representative extracted the active ingredient from the fruit of the Silybummarianum, which is named as silymarin, a new class of flavonoid having a C-9 substituents, i.e., a flavonoid lignans condensed with a dihydroflavonol and a phenylpropanoid derivative. Silibinin (silibinin) is one of the main components of silymarin. Pharmacological and toxicological studies have shown that silibinin has the effects of protecting and stabilizing the hepatocyte membrane, promoting the recovery of hepatocyte and improving the liver function. Silibinin has different levels of protection and treatment effects on various types of hepatic injury caused by hepatic poisons such as carbon tetrachloride, thioacetamide, hydroxycholine, phalloidine, mucronatine, etc. And silibinin can be used for treating acute and chronic hepatitis, early hepatocirrhosis, fatty liver, toxic or drug-induced hepatopathy.

The silibinin is poor in water solubility and common organic solvents, resulting in low bioavailability and thereby affecting the clinical efficacy. To improve the bioavailability thereof, domestic and external pharmacy workers have made substantial amounts of work. The measures to improve the absorption of poorly soluble drugs are typically superfine grinding salinization, and the addition of cosolvent, etc. In recent years, the studies have shown that the dissolution and bioavailability are greatly improved by the methods of formulating into cyclodextrin inclusion compound, solid dispersion, synthetic phospholipid complex and formulating into different dosage forms.

From the perspective of solid preparation, the phospholipid complex is a more specific solid dispersion, which has a fixed melting point, is a molecular compound (complex) whose chemical nature is more stable and different from the compound of drug and phospholipid, such compounds varies with the types of phospholipid and ratios of drug to phospholipid, and a phospholipid molecule can be bound with a different number of drug molecules. Deduced from the spectroscopy characteristics of the complex, the drug has a strong interaction with the polar groups of the phospholipid, which inhibits the free rotation of the single chains in the molecule, whereas the two long fatty acid chains of the phospholipid do not participate in the complex reaction and are free to shift and wrap the polar portions of the phospholipid to form a lipophilic surface, so that the complex shows strong lipid solubility. The complex changes the physiochemical properties of drug, and thus increases the lipid solubility of the drugs and reduces the water solubility of the drugs, and promotes the combination of drug molecules and cell membranes to improve the absorption and increases the bioavailability of the drug.

Pu'er tea is a unique and famous tea in Yunnan province. The locality has moderate climate, abundant rainfall and is mist-shrouded. Pu'er tea is divided into two series by Yunan big leaf species sun-dry tea and reprocessing thereof: the unzymic Pu'er tea by directly re-processing into the finished product and the enzymic Pu'er tea by re-processing after the artificial accelerated fermentation, and the patterns of which are divided into loose tea and compressed tea; natural aging process is also persistently carried out after the finished products, with the unique qualities gets better.

Pu'er tea is the only post-fermented tea, and substances harmful to the human body such as theophylline, tea polyphenols are degraded in the long process of fermentation, so the product is mild, does not stimulate the body, and also can promote metabolism, accelerate the digestion and transformation of fats and toxins in the body. For the problems of obesity and three-hypes which are puzzling urbanites, Pu'er tea can play a good mitigation effect, such as expelling of toxin, nourishing the stomach, anti-inflammatory, reducing the cholesterol, off lipid and removing grease, cosmetic slimming. Modern technologies show that Pu'er tea can improve insulin resistance, regulate levels of blood lipid and leptin, etc., and can block the fat accumulation of hepatic parenchymal cell caused by insulin resistance to some extent.

Non-alcoholic fatty liver disease (NAFLD) is a metabolic stress-induced hepatic injury that is closely related to insulin resistance and genetic susceptibility, the pathological changes of which are similar to alcoholic fatty liver disease. NAFLD is a clinicopathological syndrome characterized by steatosis and fat storage of hepatocytes in the hepatic lobule but without history of alcohol abuse. NAFLD shows different degrees of hepatic lesion, from simple fatty liver without any inflammation to severe inflammatory response of severe fibrosis and even cirrhosis, mainly includes 3 types: simple fatty liver, steatohepatitis, fatty cirrhosis.

Non-alcoholic Fatty Liver Disease Treatment

1. Prevention of protopathies or associated risk factors.
2. Basal treatment: developing a reasonable energy intake and diet adjustment, taking moderate aerobic exercises, correcting bad lifestyles and behaviors.
3. Avoiding aggravating hepatic injury: preventing a sharp decline in weight, drug abuse and other factors that may induce exacerbation of hepatopathy.
4. Weight loss: requiring all NAFLD patients who are overweight, and have visceral obesity and rapid weight gain in the short term to change the lifestyles to control weight and reduce waist circumference. Basal treatment for 6 months, weight loss <0.45 kg per month, or body mass index (BMI) >27 $kg/m^2$ combined with blood lipid, blood glucose, blood pressure and other indicators of more than two abnormalities may consider adding sibutramine or orlistat and other obesity drugs, weight loss per week should not exceed 1.2 Kg (children do not exceed 0.5 Kg per week); BMI >40 $kg/m^2$ or BMI >35 $kg/m^2$ combined with sleep apnea syndrome and other obesity-related diseases, may consider the proximal end gastric bypass procedures to lose weight (II-1, II-2, II-3, III).
5. Insulin sensitizer, combined with type 2 diabetes, impaired glucose tolerance, fasting plasma glucose and visceral obesity, may consider the application of metformin and thiazolidinediones in order to improve insulin resistance and control of blood glucose (II-1, II-2, II-3).
6. Hypolipidemic agents: dyslipidemia, with basal treatment and (or) application of weight loss and hypoglycemic drugs for more than 3-6 months, is still mixed with hyperlipidemia or hyperlipidemia, combined with more than 2 risk factors, should consider adding the use of fibrates, statins or probucol and other hypolipidemic drugs (II-1, II-2, II-3).
7. Drugs for hepatopathy: NAFLD associated with hepatic dysfunction, metabolic syndrome, 3-6 months after basal treatment remains ineffective, and liver biopsy shows NASH and chronic progression of the course of the disease, the drug auxiliary treatment for hepatopathy can be used with antioxidant, anti-inflammatory, anti-fibrosis, and related drugs (II-1, II-2, II-3, III) such as polyene phosphatidylcholine, vitamin E, silymarin and ursodeoxycholic acid can be rationally chosen according to drug performance, disease activity and stage of the disease, but multi-drugs should not be applied simultaneously.
8. Liver transplantation: mainly for NASH-related end-stage hepatopathy and some cryptogenic J hepatocirrhosis, and the metabolic condition (III) should be screened before liver transplantation. BMI >40 kg/m² is contraindication to liver transplantation (III).

The above treatments have not been used by being mixed together, such as a combination of hypoglycemic and hepatopathy drugs, or a combination of lipid-lowering and hepatopathy drugs. Therefore, the search for a pharmaceutical with a variety of health-promoting functions cannot wait.

SUMMARY OF THE INVENTION

In order to solve the above technical problems, the present invention provides a pharmaceutical composition and a preparation thereof which is therapeutically effective for non-alcoholic fatty liver diseases, and also has a synergistic effect on the treatment of non-alcoholic fatty liver diseases when the four are combined in use.

The present invention provides the methods for preparing the pharmaceutical composition and the preparation thereof.

The present invention is achieved by the following technical solutions:

A pharmaceutical composition is prepared from the following bulk drugs by weight ratio:
 8.75-60 parts of silibinin,
 15-65 parts of phospholipid,
 25-200 parts of Pu'er tea extract, and
 5-50 parts of radix puerariae extract.

Preferably, the pharmaceutical composition is prepared from the following bulk drugs by weight ratio:
 25-40 parts of silibinin,
 30-50 parts of phospholipid,
 80-120 parts of Pu'er tea extract, and
 10-35 parts of radix puerariae extract.

Most preferably, the pharmaceutical composition is prepared from the following bulk drugs by weight ratio:
 35 parts of silibinin,
 42 parts of phospholipid,
 100 parts of Pu'er tea extract, and
 20 parts of radix puerariae extract.

The phospholipid of the present invention is a phospholipid or lecithin, which is mainly composed of phosphatidylcholine, preferably soybean phospholipid.

The role of the phospholipid in the present invention is to promote the dissolution and absorption of pharmaceuticals, silibinin is a pharmaceutical with low solubility and low permeability, and the phospholipid is combined therewith to form a phospholipid complex so as to improve solubility of the silibinin, thereby improving the bioavailability of the pharmaceuticals.

Described silibinin and phospholipid are both known from the prior art or commercially available. In order to better exert the efficacy of the present invention, the silibinin of the present invention is preferably prepared by dissolving silymarin in 80% ethanol, filtering and washing the precipitate with 95% ethanol for three times, collecting the precipitate. The precipitate is dissolved in anhydrous ethanol, filtered, and the filtrate is added with a certain amount of water to separate out the precipitate, and the precipitate is collected by filtration, dried under reduced pressure, pulverized and mixed.

The Pu'er tea extract is commercially available, preferably a DEEPURE® Pu'er tea essence. It is also possible to be prepared according to the prior art. In order to better exert the efficacy of the present invention, Pu'er tea essence or Pu'er tea extract is preferably prepared according to the method of patents (publication No. CN101961061A, CN101961061B, CN101961425A, CN101961425B, CN101961060A, CN101961059A, CN101961059B).

For example, said Pu'er tea essence is prepared as follows:
Step 1, Pu'er tea leaves are decocted with 6-12 times the volume of water for 2-4 times, 0.5-2 hours each time; extract solution is filtered, and filtrate is concentrated under reduced pressure and the temperature of ≤70° C. to the weight of tea leaves:the volume of concentrate=1:2-1:3;
Step 2, the concentrate is centrifuged with a centrifuge, the centrifugate is concentrated under reduced pressure to density of 1.1-1.25 at 45-65° C., concentrated cream is spray dried or microwave dried to obtain the final product.

Preferably, the steps are present as follows:
Step 1, Pu'er tea leaves are decocted with 6-12 times the volume of vigorously boiling water for 3 times, 0.5-2 hours each time; extract solution is filtered, and filtrate is concentrated under reduced pressure and the temperature of ≤70° C. to the weight of tea leaves:the volume of concentrate=1:2-1:3;
Step 2, the concentrate is centrifuged with a tripod pendulum type batch centrifugal, the tripod pendulum is centrifuged with a tubular-bowl centrifuge, and the centrifugate is concentrated under reduced pressure to density of 1.1-125 at 45-65° C., concentrated cream is spray dried or microwave dried to obtain the final product;
wherein tubular-bowl centrifuge condition is: centrifuge speed: 15000-19000 rpm/min; spray drying conditions are: inlet temperature: 140-190° C., outlet temperature: 75-95° C.

Most preferably, the steps are present as follows:
Pu'er tea leaves are decocted with vigorously boiling water for 3 times, the first time decocted for 1.5 h, 10 times the volume of water added; the second time decocted for 1.5 h, 8 times the volume of water added; the third time decocted for 1 h, 8 times the volume of water added, extract solution is filtered, and filtrate is concentrated under reduced pressure and the temperature of ≤70° C. to the weight of tea leaves: the volume of concentrate=1:2-1:3, the concentrate is centrifuged with a tripod pendulum type batch centrifugal, the tripod pendulum is centrifuged with a tubular-bowl centrifuge, and the centrifugate is concentrated under reduced pressure to density of 1.1-1.25 at 45-65° C., concentrated cream is spray dried or microwave dried to obtain the final product;

wherein tubular-bowl centrifuge condition is: centrifuge speed: 15000-19000 rpm/min; spray drying conditions are: inlet temperature: 140-190° C., outlet temperature: 75-95° C.

The radix puerariae extract is commercially available for diet supplement or for pharmaceutical use, characterized in that the puerarin content is not less than 80%.

The above compositions are made by weight ratios, and may be increased or reduced according to corresponding proportion in production processes, such as large-scale production can be in unit of kg or T (ton); small scale preparations can also be in unit of g. The weight can be increased or reduced, but the proportions of the weight ratio of bulk drugs between the components remain unchanged.

The proportions of the above weight ratio are obtained through scientific screening, for special patients, such as patients with severe or mild symptom, obese or thin patients, the proportions of the amount of composition can be accordingly adjusted, increased or decreased no more than 10%, the efficacy is substantially constant.

Any pharmaceutically acceptable dosage forms can be formulated in the formulation of a pharmaceutical preparation, the dosage forms are selected from: tablet, sugar coated tablet, film coated tablet, enteric coated tablet, capsule, hard capsule, soft capsule, oral liquid, oral agent, granule, pill, powder, paste, sublimed preparation, suspension agent, solution, injection, suppository, ointment, emplastrum, creme, spray, patch. Preferably oral preparations, and optimal preferably tablet, capsule, granule.

Some pharmaceutically acceptable carriers can be added into the compositions of the present invention as needed, the pharmaceutical preparations can be prepared using galenic pharmacy conventional techniques, such as mixing the pharmaceutically active substances with pharmaceutically acceptable carriers. The pharmaceutically acceptable carriers are selected from: mannitol, sorbitol, sorbic acid or sylvite, sodium metabisulfite, sodium bisulfite, sodium thiosulfate, cysteine hydrochloride, mercaptoacetic acid, methionine, vitamin A, vitamin C, vitamin E, vitamin D, azone, disodium EDTA, calcium disodium EDTA, the carbonate, acetate, phosphate of monovalence alkali metal or aqueous solution thereof hydrochloric acid, acetic acid, sulfuric acid, phosphoric acid, amino acid, sodium chloride, potassium chloride, sodium lactate, xylitol, maltose, glucose, fructose, dextran, glycine, starch, sucrose, lactose, mannitol, silicon derivative, cellulose and derivate thereof, alginate, gelatin, polyvinyl pyrrolidone, glycerine, propylene glycol, ethanol, Tween 60-80, Span-80, beeswax, lanolin, liquid paraffin, cetyl alcohol, gallic acid esters, agar, triethanolamine, basic amino acid, urea, allantoin, calcium carbonate, calcium bicarbonate, surfactant, polyethylene glycol, cyclodextrin, beta-cyclodextrin, phospholipid material, kaolin, talc, calcium stearate, magnesium stearate, etc. Preferably, the carrier is one or more of microcrystalline cellulose, lactose, starch, sodium carboxymethylcellulose, low substituted hydroxypropyl cellulose, talc.

When the composition of the present invention is prepared into medicament, the unit dosage of the medicament may contain 0.1-1,000 mg of the pharmaceutically active substance of the present invention, and the remainders are pharmaceutically acceptable carriers. The pharmaceutically acceptable carriers may be 0-99.9% of the total preparation weight by weight. Preferably, the pharmaceutically acceptable carriers may be 40-70% of the total preparation weight by weight. The usage and dosage of the Chinese traditional medicine compositions or preparations of the present invention are determined according to the conditions of patients while being used.

The cumulative dissolution rate of the pharmaceutical composition preparations according to the present invention, such as tablets, capsules, granules and so on, is not less than 80% while dissolution in vitro for 2 h, in a dissolution condition: slurry method, rotation speed of 100 rpm and temperature of 37□, and release medium is: 1000 ml of hydrochloric acid solution at pH1.2, dosage: 1 capsule/1 tablet/1 bag granules.

A preparation method of the pharmaceutical composition of the present invention comprises the following steps:
① taking a prescription amount of raw materials for later use;
② preparation of silibinin complex liquid: weighing a prescription amount of silibinin and phospholipid, and dissolving them in the anhydrous ethanol, heating and refluxing to clarify the solution and continuing to heat for a certain time, then concentrating the clear solution under reduced pressure to a certain volume, to obtain the silibinin complex liquid for later use;
② granulation: weighing a prescription amount of Pu'er tea extract as a base material, taking the silibinin complex liquid prepared in step ② as a feed liquid, and preparing granules by a fluidization spray method with a fluidized bed, and drying after the liquid complex is all sprayed in for later use;
④ total blending: mixing a prescription amount of radix puerariae extract with the granules of step ③ uniformly in an equal incremental manner to obtain the pharmaceutical composition.

The present invention also includes a preparation step ⑤, taking the pharmaceutical composition of step ④ and pharmaceutically acceptable carriers, and preparing pharmaceutically acceptable dosage forms according to the conventional preparation process.

Further preferably, the preparation method of the pharmaceutical composition of the present invention, comprises the following steps:
① taking a prescription amount of raw materials for later use;
② preparation of silibinin complex liquid: weighing a prescription amount of silibinin and phospholipid, and dissolving them in the anhydrous ethanol, heating and refluxing to clarify the solution and continuing to heat for a certain time, then concentrating the clear solution under reduced pressure to a certain volume, to obtain the silibinin complex liquid for later use;
③ granulation: weighing a prescription amount of Pu'er tea extract as a base material, taking the silibinin complex liquid prepared in step ② as a feed liquid, and preparing granules by a fluidization spray method with a fluidized bed, and drying after the liquid complex is all sprayed in for later use;
④ total blending: mixing a prescription amount of radix puerariae extract with the granules of step ③ uniformly in an equal incremental manner to obtain the pharmaceutical composition.
⑤ preparation: taking the pharmaceutical composition and pharmaceutically acceptable carriers to prepare pharmaceutically acceptable dosage forms.

Wherein the heating time described in step ② is 0.5-1.5 hours; the concentrated volume is 5%-20% of the original volume and the temperature of concentration under reduced pressure is 60-80° C.

Wherein the parameters of the fluidized bed in step ③ are: the temperature of the materials is 40-65° C., during the granulation process, the parameters such as fan frequency, inlet air temperature and infusion frequency are adjusted to keep the materials in good fluidization state.

After completing the granulation, the granules are dried for 10-60 minutes, and the drying temperature is 55-65° C.

Pu'er tea can improve insulin resistance, regulate the levels of blood lipid and leptin and other effects, can block the fat accumulation of hepatic parenchymal cell caused by insulin resistance to a certain extent, combined with the strong free radical scavenging and anti-oxidative stress ability of silibinin, the two has preferable anti-NAFLD (non-alcohol fatty liver) effect.

Ve is added to further enhance the beauty-improving effect of the product, and L-carnitine is added to enhance the lipid-lowering and weight-controlling effects of the product.

Hereinafter, the advantageous effects of the present invention will be described by experimental examples.

Experimental Example 1 Dissolution Experiment In Vitro

The dissolutions of the silibinin-phospholipid-Pu'er tea-radix puerariae extract compositions obtained in embodiments 16-20 are determined under the following conditions: the selection of the dissolution methods is based on the properties of the main component silibinin in the compositions, silibinin, as a medicament with low solubility and low permeability, is the fourth category in the Biopharmaceutics Classification System (BCS), dissolution and absorption thereof are both the rate-limiting steps, either of which should be resolved at the same time in order to improve the bioavailability of the pharmaceuticals. Dissolution stage of the silibinin is mainly carried out in the stomach, the absorption stage is mainly carried out in the small intestine, and measuring the in-vitro dissolution of the pharmaceutical helps to improve the bioavailability of the pharmaceuticals. Therefore, the following dissolution method is chosen to evaluate the composition: slurry method, rotation speed of 100 rpm and temperature of 37° C., and release medium is: 1,000 ml of hydrochloric acid solution at pH1.2, dosage: 1 capsule/1 tablet/1 bag granules. The sampling points are: 15, 30, 45, 60, 90, 120 min. The cumulative dissolution is determined. The results are shown in Table 1 below.

The dissolution determination of the reference preparation (silibinin-phospholipid complex preparation, laboratory homemade) is carried out, and compared with the silibinin-phospholipid-Pu'er tea-radix puerariae extract compositions prepared in embodiments 16-20, and the results are as shown in FIG. 1. It can be seen from the data in Table 1 and the graph of FIG. 1:

The in-vitro release of the silibinin-phospholipid-Pu'er tea-radix puerariae extract composition prepared by the preparation method of the present invention is significantly better than that of the reference preparation silibinin-phospholipid complex, surprisingly, the cumulative dissolution of the composition in the hydrochloric acid solution at pH1.2 for 2 h reaches to more than 80%, nearly completely dissolved, which is doubled as compared with that of the reference preparation, resolving the problems of low solubility and low bioavailability of silibinin that have always existed, which will provide the basis for the studies of dose setting and in-vivo safety and efficacy of silibinin composition in the future.

Pooling the data of in-vitro dissolution experiments and in-vivo pharmacological researches, the present invention further improves the dissolution of the pharmaceutical by combining the silibinin-phospholipid complex with Pu'er tea and radix puerariae extract, by continuing the absorption improvements of the drug by increasing the compatibility of the drug and the biofilm after the combination of silibinin and phospholipid, from two aspects of improving the dissolution and absorption to improve the bioavailability of the main component silibinin.

Experimental Example 2 Evaluation of Pharmacodynamics In Vivo

1 Experimental Animals 80 mice with SPF grade and 6-week-old male C57 BL/6J leptin-deficient (ob/ob), 10 mice with SPF grade and 6 weeks old male C57 BL/6J (ob/m), provided by the Beijing Huafukang Bioscience Co., Inc., raised in Tasly Institute's pharmacological toxicology research center barrier animal room, at the temperature of 20° C.-25° C., relative humidity of 60%, 5 mice in each cage, lighting time of 12 hours, timely and quantitative feed, ob/ob mice are fed with high fat diet (HFD, D12492), C57 BL/6J mice are fed with normal diet, both are provided by Beijing Huafukang Bioscience Co., Inc., and free drinking water, daily replacement of padding.

2 Tested Substances

Silibinin-phospholipid complex, provided by Tasly Pharmaceutical Co., Ltd., lot No. 500902031. Pu'er tea extract, brown powder, supplied by Tasly Pharmaceutical Co., Ltd., lot No. Z001 PE(2014)C06(H); radix puerariae extract, provided by Shanxi Yongyuan Bio-Tech Co., Ltd., lot No. YYP140717; the above tested substances are stored in the sample cabinet of the test room of Pharmacology Institute to be protected from light at room temperature.

TABLE 1

| | Cumulative dissolubility (%) | | | | | | | |
|---|---|---|---|---|---|---|---|---|
| Time (min) | Embodiment 1 | Embodiment 16 | Embodiment 17 | Embodiment 18 | Embodiment 18 | Embodiment 20 | Embodiment 22 | Embodiment 23 |
| 15 | 18.90% | 14.45% | 8.98% | 15.06% | 9.74% | 7.11% | 7.83% | 7.08% |
| 30 | 41.28% | 39.22% | 29.40% | 55.75% | 24.11% | 36.87% | 20.19% | 26.11% |
| 45 | 69.83% | 71.98% | 37.67% | 66.24% | 51.98% | 58.33% | 49.02% | 54.26% |
| 60 | 79.42% | 78.67% | 72.90% | 69.51% | 70.34% | 75.42% | 71.90% | 78.23% |
| 90 | 83.92% | 81.92% | 78.43% | 80.96% | 78.87% | 79.21% | 81.42% | 81.38% |
| 120 | 85.98% | 82.35% | 81.11% | 81.92% | 81.38% | 82.65% | 84.38% | 86.02% |

3 Experimental Methods
3.1 Experimental Dose Design and Grouping

The silibinin-phospholipid complex is administered to the experimental animals at a daily dose of 3 g (containing silibinin 420 mg, soybean phospholipid 504 mg); the Pu'er tea extract is administered to the experimental animals at a daily dose of 1.2 g. The compatibility proportions and the experimental dose designs of the five different compositions are shown in Table 2, the dose of the experimental animals is set to the corresponding equivalent dose of the corresponding tested substances, the formula for calculation is as follows:

animal experimental dose=recommended human dose/60 kg*12.3

TABLE 2

Dose of different compositions

| | Recommended daily dosage (mg) | | | | | Experiment animal dose design (mg/kg) | | | | |
|---|---|---|---|---|---|---|---|---|---|---|
| Prescription pharmaceuticals | Combination 1 | Combination 2 | Combination 3 | Combination 4 | Combination 5 | Combination 1 | Combination 2 | Combination 3 | Combination 4 | Combination 5 |
| Silibinin | 420 | 420 | 420 | 105 | 105 | 86.10 | 86.10 | 86.10 | 21.53 | 21.53 |
| phospholipid | 504 | 780 | 780 | 195 | 195 | 103.32 | 160.00 | 160.00 | 40.00 | 40.00 |
| Pu'er tea extract | 1200 | 1200 | 2400 | 300 | 1200 | 246.00 | 246.00 | 492.00 | 61.50 | 246.00 |
| Radix puerariae extract | 240 | 240 | 60 | 120 | 120 | 49.20 | 49.20 | 12.30 | 24.60 | 24.60 |

3.2 Administration of Tested Substances

After 1 week of adaptive feeding, 80 ob/ob mice of 6-week-old are randomly divided into 8 groups: a model group, a silibinin-phospholipid complex group, a Pu'er tea extract group, a combination 1 group, a combination 2 group, a combination 3 group, a combination 4 group, and a combination 5 group, 10 mice for each group. Another 10 C57BL/6J mice of 6-week-old are in a normal group. Normal group mice are fed with normal diet, the model group and the administration group are fed with high fat diet (HFD, D12492). In addition, the mice in different drug intervention groups are given the corresponding doses of drugs by means of intragastric administration, the doses of the five compositions are shown in Table 1, the normal group and the model group are given the same amount of distilled water, continuous intragastric administration for 6 weeks.

The mice are free to eat and drink during the experiment, weekly weight, and the doses are adjusted according to the body weight After the last administration, fasting for 12 h, but water is given, weighing the body weight, extracting rats' eyeballs to collect blood and then put them to death by breaking their necks, and the liver is harvested rapidly, physiological saline rinsing, filter paper blotting and preserved in a −20° C. refrigerator after weighing.

3.3 Detecting Indicators and Methods 3.3.1 General Observation

The weights of mice in each group are measured weekly during the experiment.

3.3.2 Calculation of the Liver Index and Observation of the General Morphology of the Liver After finishing the experiment, the liver is weighed and the liver index is calculated, the liver index (%)=liver wet weight/body weight*100%.

3.3.3 Determination of Serum Biochemical Indexes

Blood of all the mice are collected by extracting rats' eyeballs and centrifuged at 3000 r/min for 15 minutes, the serum is separated and collected in an EP tube and stored at −20° C. refrigerator for later use. The content of glutamic oxaloacetic transaminase (AST), glutamicpyruvic transaminase (ALT), total cholesterol (TC), low-density lipoprotein cholesterol (LDL-C) in serum are measured by 7020 automatic biochemistry instrument.

3.3.4 Insulin Resistant Index

Serum FINS is detected using the Elisa kit and the insulin resistance index is calculated by the formula.

$$Home - IR = \frac{FBG \times FINS}{22.5}$$

3.3.5 Liver Histopathological Examination

Frozen sections are prepared from frozen liver tissues and the degree of hepatic steatosis is observed by oil red O staining. Oil red O staining operation steps: frozen slicing→sufficiently washing with distilled water→staining with oil red O diluent in the dark for 10-15 minutes→taking out 6 ml of oil red O saturated liquid, adding 4 ml of distilled water, leaving it for 5-10 minutes and filtrating for later use→differentiating to interstitial clear under mirror with 60% ethanol→washing with water→nuclear counter staining with hematoxylin→washing with water→sealing piece with neutral gum→microscope observation.

3.4 Data Processing

SPSS 15.0 statistical software is used for analysis, the data are expressed as mean±standard deviation, the t test is used to analyze whether there's any difference between the two groups before and after treatment or not, and the difference is statistically significant with $P<0.05$.

4 Experimental Results 4.1 the Effects of Each Tested Substance on Body Weight

Mice in each group are measured once a week during the experiment, and the effects of each group of medicaments on body weight of mice suffering from non-alcoholic fatty liver diseases in each group are observed. As shown in Table 3, the weight of mice in normal group is increased slowly and the weight of mice in model group is increased more rapidly. After 6 weeks of administration, the other administration groups except for the silibinin-phospholipid complex group could inhibit the weight increases of mice in different degrees ($P<0.05$), a combined use of silibinin-phospholipid complex, Pu'er tea extract and radix puerariae extract is significantly superior to using silibinin alone.

TABLE 3

Effect of test substances on body weight of mice (g, n = 10, x̄ ± S)

| Group | Body weight (g) | | | |
|---|---|---|---|---|
| | Before administration | Week 2 after administration | Week 4 after administration | Week 6 after administration |
| Normal | 24.36 ± 1.64 | 26.64 ± 2.50 | 27.65 ± 1.54 | 28.02 ± 2.03 |
| Model | 49.88 ± 3.51 | 56.53 ± 2.12 | 60.15 ± 2.55 | 62.87 ± 2.75 |
| Silibinin-phospholipid complex | 49.55 ± 3.23 | 55.57 ± 4.13 | 59.66 ± 5.00 | 63.10 ± 4.83 |
| Combination 1 | 50.43 ± 3.72 | 51.07 ± 2.56** | 53.10 ± 4.06** | 55.25 ± 4.20** |
| Combination 2 | 49.90 ± 3.53 | 53.87 ± 3.64* | 56.56 ± 4.77* | 59.74 ± 3.61* |
| Combination 3 | 49.75 ± 4.00 | 53.82 ± 3.50* | 54.80 ± 3.37** | 59.64 ± 2.72* |
| Combination 4 | 50.52 ± 3.71 | 50.98 ± 2.76** | 52.01 ± 4.25** | 54.16 ± 4.32** |
| Combination 5 | 50.88 ± 4.18 | 51.91 ± 2.83** | 53.44 ± 3.56** | 55.71 ± 3.88** |

*compared with the model group $P < 0.05$;
**compared with the model group $P < 0.01$;

4.2 the Effects of Each Tested Substance on Liver Index

As shown in Table 4, the body weight, liver wet weight and liver index of mice in the model group are significantly increased compared with the normal group (P<0.01), and the silibinin-phospholipid complex can decrease the wet weight of the liver and liver index (P<0.05), but has no significant effect on body weight of the mice (P>0.05); all the five compositions of silibinin-phospholipid complex, Pu'er tea extract and radix puerariae extract can significantly reduce the wet weight and liver index of the liver of mice (P<0.05), the effect of a combined use of the three is significantly better than that of using the silibinin-phospholipid complex alone.

As shown in Table 5, the levels of serum TC, LDL, ALT, AST and insulin resistance index are significantly increased in non-alcoholic fatty liver model mice compared with the normal group (P<0.05); there is no significant improvement in the abnormal elevation of the silibinin-phospholipid complex (P>0.05); the silibinin-phospholipid complex, Pu'er tea extract and radix puerariae extract compatibility group of different proportions can significantly reduce TC, LDL-C, ALT, AST and insulin resistance indexes (P<0.05), and the effect is better than that of using the silibinin-phospholipid complex alone.

TABLE 4

Effects of each tested substance on liver index of mice

| Group | Body weight (g) | Liver wet weight (g) | Liver mass index % |
|---|---|---|---|
| Normal | 28.16 ± 2.09 | 1.096 ± 0.106 | 3.927 ± 0.604 |
| Model | 62.77 ± 2.68 | 4.328 ± 0.297 | 6.902 ± 0.492 |
| Silibinin-phospholipid complex | 63.66 ± 5.04 | 3.997 ± 0.376* | 6.302 ± 0.670* |
| Combination 1 | 54.00 ± 2.23** | 2.636 ± 0.421** | 4.843 ± 0.792* |
| Combination 2 | 59.29 ± 3.73* | 3.462 ± 0.675** | 5.922 ± 1.171** |
| Combination 3 | 58.43 ± 3.88** | 3.000 ± 0.710** | 5.158 ± 1.267** |
| Combination 4 | 51.07 ± 2.98** | 2.436 ± 0.382** | 4.775 ± 0.716** |
| Combination 5 | 53.77 ± 2.14** | 2.736 ± 0.230** | 5.096 ± 0.470** |

*compared with the model group $P < 0.05$;
**compared with the model group $P < 0.01$;

4.3 Effects of Each Tested Substance on Blood Lipid, Liver Function and Insulin Resistance Indexes of Mice

TABLE 5

Effects of each tested substance on blood lipid, liver function and insulin resistance indexes of mice

| Group | TC | LDL-C | ALT | AST |
|---|---|---|---|---|
| Normal | 2.99 ± 0.25 | 0.26 ± 0.03 | 51.93 ± 20.99 | 118.62 ± 44.42 |
| Model | 10.41 ± 1.18 | 2.33 ± 0.54 | 425.48 ± 90.03 | 205.61 ± 22.74 |
| Silibinin-phospholipid complex | 10.35 ± 1.12 | 2.22 ± 0.32 | 374.34 ± 56.78 | 182.61 ± 28.50 |
| Combination 1 | 7.14 ± 0.96** | 1.13 ± 0.20** | 236.70 ± 92.42** | 123.30 ± 24.39** |
| Combination 2 | 9.31 ± 1.02* | 1.69 ± 0.29* | 331.35 ± 98.22* | 178.31 ± 29.61* |
| Combination 3 | 8.86 ± 1.21* | 1.54 ± 0.35** | 321.69 ± 112.79* | 163.28 ± 34.78* |
| Combination 4 | 6.08 ± 1.12** | 1.03 ± 0.25** | 181.61 ± 46.79** | 126.30 ± 35.62** |
| Combination 5 | 7.34 ± 0.94** | 1.15 ± 0.18** | 247.81 ± 87.55** | 138.30 ± 34.07** |

*compared with the model group $P < 0.05$;
**compared with the model group $P < 0.01$;

4.4 Effects of Each Tested Substance on Liver Pathology of Mice

Oil red O staining: according to the size and number of red particles in hepatocytes of liver frozen issues stained by Oil red O under light microscope, it is divided into mild, moderate and severe type. Mild, that is, 1/3-2/3 of red granules are shown per unit area under light microscope, graded as 1 point; moderate, that is, more than 2/3 of the hepatocytes containing red particles, graded as 2 points; severe, that is, almost all of the hepatocytes containing red particles, graded as 3 points; no steatosis is observed, graded as 0 points.

As shown in Table 6, steatosis occurred in nearly all the hepatocytes in the liver tissues of the model group, and the pathological scores are significantly increased than that in the normal group ($P<0.01$); there is no significant improvement on liver pathological scores by using silibinin-phospholipid complex or Pu'er tea extract alone ($P>0.05$); the combination of different proportions of the Pu'er tea extract, silibinin-phospholipid complex and radix puerariae extract can significantly improve the liver steatosis, reduce the pathological scores ($P<0.05$), and the effect is better than that of using the silibinin-phospholipid complex and the Pu'er tea extract alone.

TABLE 6

Effects of each tested substance on liver pathology of mice

| Group | Oil red O staining pathological score |
|---|---|
| Normal | 0.000 ± 0.000 |
| Model | 2.667 ± 0.707 |
| Silibinin-phospholipid complex | 2.444 ± 0.726 |
| Pu'er tea extract | 2.200 ± 0.919 |
| Combination 1 | 1.889 ± 0.601* |
| Combination 2 | 2.000 ± 0.535* |
| Combination 3 | 2.000 ± 0.500* |
| Combination 4 | 1.778 ± 0.833* |
| Combination 5 | 1.900 ± 0.568* |

*compared with the model group $P < 0.05$;
**compared with the model group $P < 0.01$;

5 Experimental Conclusions

The above experimental results show that: the body weight, liver index, blood lipid, ALT, AST and insulin resistance index are significantly increased in the mice of the non-alcoholic fatty liver model group compared with those in the blank group, and the liver tissues are severe steatosis. Pu'er tea can improve insulin resistance, regulate blood lipids, radix puerariae has blood lipid-regulating and anti-inflammatory effects, and can also improve detoxification function of the liver and repair damaged liver cells; while silibinin has strong free radical scavenging and anti-oxidative stress ability, the combination use of the three has a significant improvement in liver steatosis and preventive and therapeutic effect on non-alcoholic fatty liver.

BRIEF DESCRIPTION OF THE DRAWINGS

FIG. 1 is an in-vitro release curve, wherein, each sample is reference preparation of Shui Lin Jia, Shui Lin Jia without Pu'er tea, and silibinin-phospholipid-Pu'er tea compositions prepared in embodiments 16-20.

DETAILED DESCRIPTION OF THE INVENTION

The present invention is further illustrated by the following specific examples, but not intended to limit the present invention.

Embodiment 1

Taking 26.25 g of silibinin, 45 g of soybean phospholipid, 75 g of Pu'er tea extract, and 15 g of radix puerariae extract.

① Preparation of silibinin complex liquid: weighing a prescription amount of silibinin, soybean phospholipid, and dissolving them in the anhydrous ethanol, heating and refluxing to clarify the solution and continuing to heat for 1 h, then concentrated under reduced pressure and recycling the ethanol to 15% of the original volume for later use;

② Granulation: weighing a prescription amount of Pu'er tea extract as a base material, taking the silibinin complex liquid prepared in step ① as a feed liquid, preparing the granules by a fluidization spray method with a fluidized bed, controlling the temperature of materials at 40° C., drying at 60° C. for 20 min after the liquid complexes are all sprayed in for later use;

③ Mixing a prescription amount of radix puerariae extract and the granules prepared in step ② uniformly in an equal incremental manner, bagging, made into 1,000 bags of granules.

Embodiment 2

Taking 180 g of silibinin, 195 g of soybean phospholipid, 600 g of Pu'er tea extract, and 150 g of radix puerariac extract.

① Preparation of silibinin complex liquid: weighing a prescription amount of silibinin, soybean phospholipid, and dissolving them in the anhydrous ethanol, heating and refluxing to clarify the solution and continuing to heat for 1.5 h, then concentrated under reduced pressure and recycling the ethanol to 20% of the original volume for later use;

② Granulation: weighing a prescription amount of Pu'er tea extract as a base material, taking the silibinin composite liquid prepared in step ① as a feed liquid, preparing the granules by a fluidization spray method with a fluidized bed, controlling the temperature of materials at 65° C., drying at 65° C. for 60 min after the liquid complexes are all sprayed in for later use;

③ Mixing a prescription amount of radix puerariac extract and the granules prepared in step ② uniformly in an equal incremental manner, bagging, made into 1,000 bags of granules.

Embodiment 3

Taking 26.25 g of silibinin, 195 g of phospholipid, 600 g of Pu'er tea extract, and 15 g of radix puerariae extract.

① Preparation of silibinin complex liquid: weighing a prescription amount of silibinin, soybean phospholipid, and dissolving them in the anhydrous ethanol, heating and refluxing to clarify the solution and continuing to heat for 0.5 h, then concentrated under reduced pressure and recycling the ethanol to 5% of the original volume for later use;

② Granulation: weighing a prescription amount of Pu'er tea extract as a base material, taking the silibinin composite liquid prepared in step ① as a feed liquid, preparing the granules by a fluidization spray method with a fluidized bed, controlling the material temperature at 50° C., drying at 55° C. for 10 min after the liquid complexes are all sprayed in for later use;

③ Mixing a prescription amount of radix puerariae extract and the granules prepared in step ② uniformly in an equal incremental manner, bagging, made into 1,000 bags of granules.

Embodiment 4

Taking 26.25 g of silibinin, 195 g of phospholipid, 75 g of Pu'er tea extract and 150 g of radix puerariae extract, and preparing 1,000 bags of granules according to the method of Embodiment 1.

Embodiment 5

Taking 180 g of silibinin, 45 g of phospholipid, 75 g of Pu'er tea extract and 15 g of radix puerariae extract, and preparing 1,000 bags of granules according to the method of Embodiment 1.

Embodiment 6

Taking 180 g of silibinin, 45 g of phospholipid, 600 g of Pu'er tea extract and 150 g of radix puerariae extract, and preparing 1,000 bags of granules according to the method of Embodiment 1.

Embodiment 7

Taking 180 g of silibinin, 195 g of phospholipid, 75 g of Pu'er tea extract and 150 g of radix puerariae extract, and preparing 1,000 bags of granules according to the method of Embodiment 1.

Embodiment 8

Taking 26.25 g of silibinin, 48.75 g of phospholipid, 75 g of Pu'er tea extract and 30 g of radix puerariae extract, and preparing 1,000 bags of granules according to the method of Embodiment 1.

Embodiment 9

Taking 26.25 g of silibinin, 48.75 g of phospholipid, 300 g of Pu'er tea extract and 30 g of radix puerariae extract, and preparing 1,000 bags of granules according to the method of Embodiment 1.

Embodiment 10

Taking 52.5 g of silibinin, 97.5 g of phospholipid, 300 g of Pu'er tea extract and 7.5 g of radix puerariae extract, and preparing 1,000 bags of granules according to the method of Embodiment 1.

Embodiment 11

Taking 75 g of silibinin, 90 g of phospholipid, 240 g of Pu'er tea extract and 36 g of radix puerariae extract, and preparing 1,000 bags of granules according to the method of Embodiment 1.

Embodiment 12 Preparation of the Composition

Taking 90 g of silibinin, 108 g of phospholipid, 270 g of Pu'er tea extract and 90 g of radix puerariae extract, and preparing 1,000 bags of granules according to the method of Embodiment 1.

Embodiment 13 Preparation of the Composition

Taking 105 g of silibinin, 126 g of phospholipid, 300 g of Pu'er tea extract and 60 g of radix puerariae extract, and preparing 1,000 bags of granules according to the method of Embodiment 1.

Embodiment 14 Preparation of the Composition

Taking 105 g of silibinin, 126 g of phospholipid, 300 g of Pu'er tea extract and 60 g of radix puerariae extract, and preparing 1,000 bags of granules according to the method of Embodiment 1.

Embodiment 15 Preparation of the Composition

Taking 120 g of silibinin, 150 g of phospholipid, 360 g of Pu'er tea extract and 105 g of radix puerariae extract, and preparing 1,000 bags of granules according to the method of Embodiment 1.

Embodiment 16

Taking the granules of Embodiment 8, adding 556 g of microcrystalline cellulose and 64 g of sodium carboxymethyl starch, mixing uniformly, encapsulated into capsules to obtain 1,000 capsules.

Embodiment 17

Taking the granules of Embodiment 9, adding 331 g of microcrystalline cellulose and 64 g of sodium carboxymethyl starch, mixing uniformly, encapsulated into capsules to obtain 1,000 capsules.

Embodiment 18

Taking the granules of Embodiment 10, adding 311 g of microcrystalline cellulose and 32 g of sodium carboxymethyl starch, mixing uniformly, encapsulated into capsules to obtain 1,000 capsules.

Embodiment 19

Taking the granules of Embodiment 13, adding 145 g of microcrystalline cellulose and 64 g of sodium carboxymethyl starch, mixing uniformly, encapsulated into capsules to obtain 1,000 capsules.

Embodiment 20

Taking the granules of Embodiment 14, adding 76 g of microcrystalline cellulose and 64 g of sodium carboxymethyl starch, mixing uniformly, encapsulated into capsules to obtain 1,000 capsules.

Embodiment 21

Taking the composition of Embodiment 8, adding 400 g of lactose, 156 g of starch, and 64 g of sodium carboxymethyl starch, mixing uniformly, encapsulated into capsules to obtain 1,000 capsules.

Embodiment 22

Taking the composition of Embodiment 13, adding 115 g of lactose, 10 g of talc powder, and 84 g of low-substituted hydroxypropyl cellulose, mixing uniformly, encapsulated into capsules to obtain 1,000 capsules.

Embodiment 23

Taking the composition of Embodiment 13, adding 145 g of microcrystalline cellulose and 64 g of sodium carboxymethyl starch, mixing uniformly, encapsulated into No. 0 capsules to obtain 1,000 capsules.

The invention claimed is:

1. A pharmaceutical composition comprising
   8.75-60 parts by weight of silibinin;
   15-65 parts by weight of phospholipid;
   25-200 parts by weight of Pu'er tea extract; and
   5-50 parts by weight of radix puerariae extract.

2. The pharmaceutical composition of claim 1 comprising
   25-40 parts by weight of silibinin;
   30-50 parts by weight of phospholipid;
   80-120 parts by weight of Pu'er tea extract; and
   10-35 parts by weight of radix puerariae extract.

3. The pharmaceutical composition of claim 1 comprising
   35 parts by weight of silibinin;
   42 parts by weight of phospholipid;
   100 parts by weight of Pu'er tea extract; and
   20 parts by weight of radix puerariae extract.

4. The pharmaceutical composition of claim 1, wherein puerarin in the radix puerariae extract is not less than 80%.

5. A pharmaceutical preparation comprising the pharmaceutical composition according to claim 1, further comprising pharmaceutically acceptable carriers;
   wherein the pharmaceutically acceptable carriers are 0.1-99.9% of the total preparation by weight.

6. The pharmaceutical preparation according to claim 5, wherein the pharmaceutically acceptable carriers are selected from the group consisting of sorbitol, sorbic acid or sylvite, sodium metabisulfite, sodium bisulfite, sodium thiosulfate, cysteine hydrochloride, mercaptoacetic acid, methionine, vitamin A, vitamin C, vitamin E, vitamin D, azone, disodium EDTA, calcium disodium EDTA, hydrochloric acid, acetic acid, sulfuric acid, phosphoric acid, amino acid, sodium chloride, potassium chloride, sodium lactate, xylitol, maltose, glucose, fructose, dextran, glycine, starch, sucrose, lactose, mannitol, silicon derivative, cellulose and derivate thereof, alginate, gelatin, polyvinyl pyrrolidone, glycerine, propylene glycol, ethanol, polysorbate 60-80, sorbitan monooleate, beeswax, lanolin, liquid paraffin, cetyl alcohol, gallic acid esters, agar, triethanolamine, basic amino acid, urea, allantoin, calcium carbonate, calcium bicarbonate, surfactant, polyethylene glycol, cyclodextrin, beta-cyclodextrin, phospholipid, kaolin, talc, calcium stearate, magnesium stearate, microcrystalline cellulose, and a carbonate, acetate, or phosphate salt of a monovalent alkali metal or aqueous solution thereof.

7. The pharmaceutical preparation according to claim 5, wherein the pharmaceutical preparation is selected from the group consisting of tablet, sugar coated tablet, film coated tablet, enteric coated tablet, capsule, hard capsule, soft capsule, oral liquid, oral agent, granule, pill, powder, paste, sublimed preparation, supensoid agent, solution, injection, suppository, ointment, emplastrum, creme, spray, and patch.

8. The pharmaceutical composition of claim 2, wherein puerarin in the radix puerariae extract is not less than 80%.

9. A pharmaceutical preparation comprising the pharmaceutical composition according to claim 2, further comprising pharmaceutically acceptable carriers;
wherein the pharmaceutically acceptable carriers are 0.1-99.9% of the total preparation by weight.

10. The pharmaceutical preparation according to claim 9, wherein the pharmaceutically acceptable carriers are selected from the group consisting of sorbitol, sorbic acid or sylvite, sodium metabisulfite, sodium bisulfite, sodium thiosulfate, cysteine hydrochloride, mercaptoacetic acid, methionine, vitamin A, vitamin C, vitamin E, vitamin D, azone, disodium EDTA, calcium disodium EDTA, hydrochloric acid, acetic acid, sulfuric acid, phosphoric acid, amino acid, sodium chloride, potassium chloride, sodium lactate, xylitol, maltose, glucose, fructose, dextran, glycine, starch, sucrose, lactose, mannitol, silicon derivative, cellulose and derivate thereof, alginate, gelatin, polyvinyl, pyrrolidone, glycerine, propylene glycol, ethanol, polysorbate 60-80, sorbitan monooleate, beeswax, lanolin, liquid paraffin, cetyl alcohol, gallic acid esters, agar, triethanolamine, basic amino acid, urea, allantoin, calcium carbonate, calcium bicarbonate, surfactant, polyethylene glycol, cyclodextrin, beta-cyclodextrin, phospholipid, kaolin, talc, calcium stearate, magnesium stearate, microcrystalline cellulose, and a carbonate, acetate, or phosphate salt of a monovalent alkali metal or aqueous solution thereof.

11. The pharmaceutical preparation according to claim 9, wherein the pharmaceutical preparation is selected from the group consisting of tablet, sugar coated tablet, film coated tablet, enteric coated tablet, capsule, hard capsule, soft capsule, oral liquid, oral agent, granule, pill, powder, paste, sublimed preparation, supensoid agent, solution, injection, suppository, ointment, emplastrum, creme, spray, and patch.

12. The pharmaceutical composition of claim 3, wherein puerarin in the radix puerariae extract is not less than 80%.

13. A pharmaceutical preparation comprising the pharmaceutical composition according to claim 3, further comprising pharmaceutically acceptable carriers;
wherein the pharmaceutically acceptable carriers are 0.1-99.9% of the total preparation by weight.

14. The pharmaceutical preparation according to claim 13, wherein the pharmaceutically acceptable carriers are selected from the group consisting of sorbitol, sorbic acid or sylvite, sodium metabisulfite, sodium bisulfite, sodium thiosulfate, cysteine hydrochloride, mercaptoacetic acid, methionine, vitamin A, vitamin C, vitamin E, vitamin D, azone, disodium EDTA, calcium disodium EDTA, hydrochloric acid, acetic acid, sulfuric acid, phosphoric acid, amino acid, sodium chloride, potassium chloride, sodium lactate, xylitol, maltose, glucose, fructose, dextran, glycine, starch, sucrose, lactose, mannitol, silicon derivative, cellulose and derivate thereof, alginate, gelatin, polyvinyl pyrrolidone, glycerine, propylene glycol, ethanol, polysorbate 60-80, sorbitan monooleate, beeswax, lanolin, liquid paraffin, cetyl alcohol, gallic acid esters, agar, triethanolamine, basic amino acid, urea, allantoin, calcium carbonate, calcium bicarbonate, surfactant, polyethylene glycol, cyclodextrin, beta-cyclodextrin, phospholipid, kaolin, talc, calcium stearate, magnesium stearate, microcrystalline cellulose, and a carbonate, acetate, or phosphate salt of a monovalent alkali metal or aqueous solution thereof.

15. The pharmaceutical preparation according to claim 13, wherein the pharmaceutical preparation is selected from the group consisting of tablet, sugar coated tablet, film coated tablet, enteric coated tablet, capsule, hard capsule, soft capsule, oral liquid, oral agent, granule, pill, powder, paste, sublimed preparation, supensoid agent, solution, injection, suppository, ointment, emplastrum, creme, spray, and patch.

16. A method of preparing the pharmaceutical preparation according to claim 5, comprising:
(1) taking a prescription amount of raw materials;
(2) preparing a silybin complex liquid by weighing a prescription amount of silybin and phospholipid, and dissolving them in the anhydrous ethanol, heating and refluxing to clarify the solution, then concentrating the clear solution under reduced pressure to a concentrated volume, to obtain the silybin complex liquid;
(3) granulating by spraying a prescription amount of Pu'er tea extract with the silybin complex liquid by a fluidization spray method with a fluidized bed, and drying;
(4) blending by mixing radix puerariae extract and the granules of step (3) uniformly to obtain the pharmaceutical composition; and
(5) combining the pharmaceutical composition with pharmaceutically acceptable carriers.

17. The method according to claim 16, wherein the heating time in step (2) is 0.5-1.5 hours; the concentrated volume is 5%-20% of the original volume and the temperature of the concentration under reduced pressure is 60-80° C.; the parameters of the fluidized bed in step (3) are that the temperature of the materials is 40-65° C., and adjusting fan frequency, inlet air temperature and infusion frequency to keep the materials in a good fluidization state during the granulation process; and wherein after the granulation is completed, the granules are dried for 10-60 minutes at 55-65° C.

18. A method of treatment, comprising administering a therapeutically effective amount of the pharmaceutical composition of claim 1 to a subject in need thereof, wherein the treatment is for non-alcoholic fatty liver disease, reducing fat, losing weight, or beautifying skin.

19. A method of treatment, comprising administering a therapeutically effective amount of the pharmaceutical composition of claim 5 to a subject in need thereof, wherein the treatment is for non-alcoholic fatty liver disease, reducing fat, losing weight, or beautifying skin.

20. A method of preparing the pharmaceutical preparation according to claim 9, comprising:
(1) taking a prescription amount of raw materials;
(2) preparing a silybin complex liquid by weighing a prescription amount of silybin and phospholipid, and dissolving them in the anhydrous ethanol, heating and refluxing to clarify the solution, then concentrating the clear solution under reduced pressure to a concentrated volume, to obtain the silybin complex liquid;

(3) granulating by spraying a prescription amount of Pu'er tea extract with the silybin complex liquid by a fluidization spray method with a fluidized bed, and drying;

(4) blending by mixing radix puerariae extract and the granules of step (3) uniformly to obtain the pharmaceutical composition; and (5) combining the pharmaceutical composition with pharmaceutically acceptable carriers;

wherein the heating time in step (2) is 0.5-1.5 hours; the concentrated volume is 5%-20% of the original volume and the temperature of the concentration under reduced pressure is 60-80° C.; the parameters of the fluidized bed in step (3) are that the temperature of the materials is 40-65° C., and adjusting fan frequency, inlet air temperature and infusion frequency to keep the materials in a good fluidization state during the granulation process; and wherein after the granulation is completed, the granules are dried for 10-60 minutes at 55-65° C.

* * * * *